United States Patent [19]

Goldberg et al.

[11] 4,454,140

[45] Jun. 12, 1984

[54] NASAL ADMINISTRATION OF DEXTROMETHORPHAN

[75] Inventors: Arthur H. Goldberg, Montclair, N.J.; Meyer Matluck, Flushing, N.Y.; Joseph A. Ranucci, North Caldwell, N.J.

[73] Assignee: Hoffmann-La Roche Inc., Nutley, N.J.

[21] Appl. No.: 415,209

[22] Filed: Sep. 7, 1982

[51] Int. Cl.³ .......................................... A61K 31/485
[52] U.S. Cl. .................................................... 424/260
[58] Field of Search ........................................ 424/260

[56] References Cited

PUBLICATIONS

Handbook of Nonprescription Drugs, 5th Ed., 1977, pp. 97–104.
The Merck Index, 9th Ed., 1976, p. 1053, § 7908.

*Primary Examiner*—Leonard Schenkman
*Attorney, Agent, or Firm*—Jon S. Saxe; George M. Gould; John J. Maitner

[57] ABSTRACT

The invention relates to a novel method of administering dextromethorphan, a known anti-tussive agent used for the suppresion of coughs due to colds and allergies. The novel method utilizes dosage forms of dextromethorphan which are adapted for nasal administration.

6 Claims, 1 Drawing Figure

NASAL ADMINISTRATION OF DEXTROMETHORPHAN

BACKGROUND OF THE INVENTION

Dextromethorphan is a known anti-tussive agent and is widely used for the suppression of cough due to colds and allergies. The common mode for administering dextromethorphan is by oral administration. When the drug is administered orally, there is variation in the absorption and bioavailability. There exists the need for an improved delivery of dextromethorphan and a dosage form which will provide enhanced bioavailability and absorption of dextromethorphan.

DETAILED DESCRIPTION OF THE INVENTION

Figure 1:
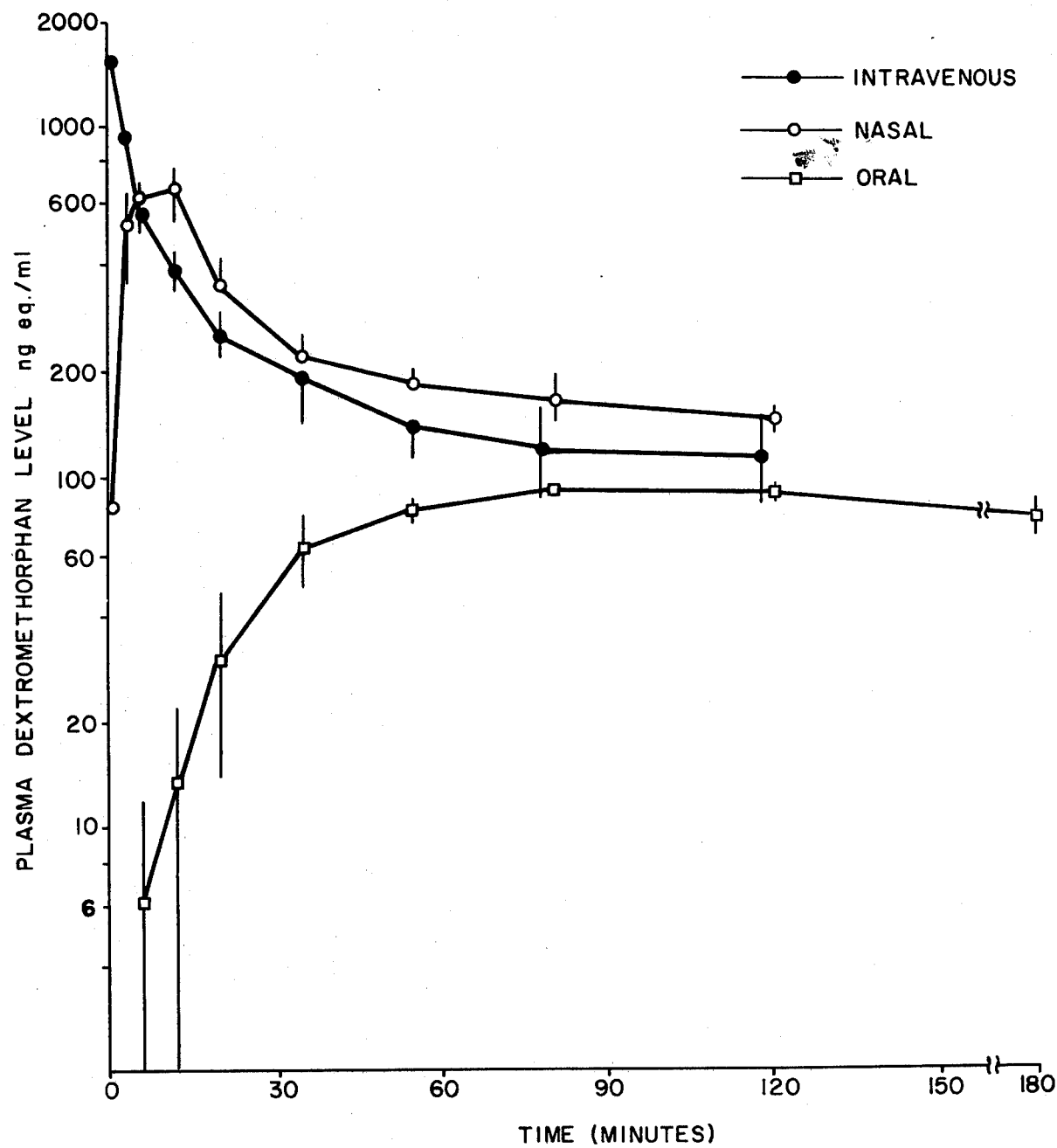

Nasal administration of dextromethorphan provides for a more rapid and more complete absorption of the drug than the standard oral route.

Dextromethorphan, or d-3-methoxy-N-methylmorphinan, can be represented by the formula

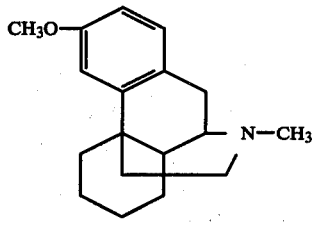

As used herein, the term "dextromethorphan" encompasses the free base or a pharmaceutically acceptable acid addition salt thereof. The preparation of the free base and pharmaceutically acceptable acid addition salts thereof is set forth in Schnider, et al., U.S. Pat. No. 2,676,177.

The term "pharmaceutically acceptable acid addition salt" denotes salts derived from inorganic acids, such as hyrochloric acid, hydrobromic acid sulfuric acid and the like, and organic acids such as acetic acid, citric acid, lactic acid, maleic acid, salicylic acid, succinic acid, and the like. The preferred salt is the hydrobromide salt.

According to the present invention, it has been found that dextromethorphan can be administered nasally with results considerably superior to those obtained with oral administration. The following study was undertaken to determine the bioavailability of dextromethorphan from nasal solution in comparison with the bioavailability of the drug when administered orally and intravenously.

Three female beagle dogs weighing about 10 kg each were used for the study without fasting. For nasal administration, the dogs were anaesthetized with an intravenous injection of 30 mg/kg of sodium pentobarbital, and 0.5 ml of a warm saline solution containing dextromethorphan (30 mg/ml) was then administered to the nasal cavity through the nostrils with a syringe. For oral administration, the dogs were not anaesthetized and 10 ml of a saline solution containing dextromethorphan hydrobromide (1.5 mg/ml) was administered via a stomach tube. For intravenous administration, the dogs were anaesthetized as noted above, and one ml of a saline solution containing dextromethorphan hydrobromide (15 mg/ml) was injected through the cubital vein.

After nasal, oral, and intravenous administration, blood was sampled from the cubital vein periodically. The blood sample, was centrifuged and 2.5 ml of plasma were analyzed. Plasma levels of dextromethorphan were determined spectrofluorophotometrically by a modification of the method of Ramachander, et al., J. Pharm. Sci., 66, 1047 (1977). Specifically, plasma was transferred into a glass tube, 0.5 ml of a saturated solution of sodium carbonate and 10 ml of ethyl acetate were added, and the contents shaken well. After centrifuging, an aliquot (8 ml) of the supernate was transferred into a glass tube containing 1.5 ml of 1.0N HCl, and was extracted into the acid layer after mixing well and centrifuging. The fluorescence of the acid layer was determined by a spectrofluorophotometer, Aminco-Bowman Ratio II, American Instrument Co. The excitation and emission wave lengths were 278 nm and 306 nm, respectively. Recovery of known amounts of dextromethorphan spiked with dog plasma was 50% of the added concentration. For calculating the drug plasma level, the above correction factor was taken into consideration.

FIG. 1 shows the mean blood levels of dextromethorphan for the study described above.

As can be seen from FIG. 1, the blood level after nasal administration of a 15 mg dose of dextromethorphan hydrobromide gave blood levels comparable to an injected dose over a period of about 5 minutes to about 2 hours, whereas oral administration of the same dosage level results in considerably lower blood levels.

Table I reports the plasma concentration of dextromethorphan after nasal, intravenous, and oral administration of 15 mg/dog of dextromethorphan hydrobromide salt.

TABLE I

PLASMA CONCENTRATION OF DEXTROMETHORPHAN AFTER INTRAVENOUS, NASAL, AND ORAL ADMINISTRATION (HBr Salt, 15 mg/dog) in Female Dog

| | Plasma Concentration ng eq./ml | | | | | | | | |
|---|---|---|---|---|---|---|---|---|---|
| | Intravenous | | | Nasal | | | Oral | | |
| | #1 | #2 | #3 | #1 | #2 | #3 | #1 | #2 | #3 |
| 1 | 1534.9 | 1588.4 | 1490.7 | 72.1 | 89.1 | 84.2 | 0 | 0 | 0 |
| 3 | 927.2 | 952.3 | 907.2 | 322.7 | 793.3 | 427.7 | 0 | 0 | 0 |
| 6 | 707.9 | 532.4 | 430.3 | 618.3 | 733.2 | 493.3 | 0 | 18.5 | 0 |
| 12 | 482.3 | 349.0 | 322.0 | 683.6 | 888.2 | 384.6 | 0 | 40.0 | 0 |
| 20 | 330.8 | 228.7 | 187.0 | 502.8 | 259.7 | 263.1 | 7.5 | 62.9 | 18.4 |
| 35 | 295.8 | 165.5 | 102.2 | 276.3 | 200.7 | 165.4 | 43.4 | 94.4 | 47.6 |
| 55 | 171.0 | 145.5 | 81.4 | 239.6 | 170.0 | 129.4 | 73.6 | 92.3 | 65.0 |
| 80 | 134.3 | 164.8 | 46.2 | 201.2 | 183.4 | 93.3 | 80.1 | 86.8 | 95.5 |
| 120 | 143.6 | 140.8 | 37.3 | 153.7 | 140.8 | 108.3 | 74.7 | 86.0 | 91.5 |

TABLE I-continued

PLASMA CONCENTRATION OF DEXTROMETHORPHAN AFTER
INTRAVENOUS, NASAL, AND ORAL ADMINISTRATION
(HBr Salt, 15 mg/dog) in Female Dog

| | Plasma Concentration ng eq./ml | | | | | | | | |
|---|---|---|---|---|---|---|---|---|---|
| | Intravenous | | | Nasal | | | Oral | | |
| | #1 | #2 | #3 | #1 | #2 | #3 | #1 | #2 | #3 |
| 180 | — | — | — | — | — | — | 63.3 | 85.7 | 53.4 |

Table II below summaries the relative bioavailabilities of dextromethorphan for nasal, intravenous, and oral administration over 0-120 minutes after dosing.

As can be seen from Table II, the total availability of the nasal dosage is from 3 to 4 times that of the oral dosage during the first 2 hours after administration.

TABLE II

RELATIVE BIOAVAILABILITIES OF
DEXTROMETHORPHAN FOR INTRAVENOUS,
NASAL AND ORAL ROUTES OVER
THE 0-120 MINUTES AFTER DOSING

| Route | AUC 0-120 min. (ng eq. ml$^{-1}$ min) | | Relative Bioavailability (0-120 min. %) |
|---|---|---|---|
| | Individual AUC | Average ± S.E. | |
| Intravenous | 32231.1 | 25832.4 ± 4295.52 | — |
| | 27597.7 | | |
| | 17668.5 | | |
| Nasal | 34103.7 | 28326.0 ± 4207.41 | 109.7 |
| | 30735.4 | | |
| | 20139.0 | | |
| Oral | 6598.7 | 7798.9 ± 815.91 | 30.2 |
| | 9356.5 | | |
| | 7441.6 | | |

Dextromethorphan hydrobromide can be conveniently administered nasally to warm-blooded animals by formulating it into a nasal dosage form comprising dextromethorphan and a non-toxic pharmaceutically acceptable nasal carrier therefor. Dextromethorphan can be employed in the form of the free base or in the form of a pharmaceutically acceptable salt thereof, e.g. dextromethorphan hydrobromide. Suitable non-toxic, non-irritating, pharmaceutically acceptable nasal carriers will be apparent to those skilled in the art of nasal pharmaceutical formulations.

Examples of pharmaceutically acceptable nasal carriers include water; physiological saline solution; alcohols, such as ethanol and isopropanol; glycols, such as propylene glycol; glycol ethers, such as polyethylene glycols which are polymers of ethylene oxide and water, represented by the formula $H(OCH_2CH_2)_nOH$, wherein n varies from 5-10.

Minor amounts of other ingredients, such as buffers, preservatives, osmotic agents, gelling agents, wetting agents, may also be present. Examples of buffers which can be employed in the compositions of this invention are: glycine; citric acid and alkali salts thereof; acetic acid and alkali salts thereof; phosphoric acid and alkali salts thereof; gluconic acid and alkali salts thereof; sodium hydroxide and potassium hydroxides. Preservatives useful in the compositions include: benzalkonium chloride, cetalkonium chloride, cetyl pyridinium chloride, cetyl trimethyl ammonium bromide, chlorobutanol, methyl paraben, propyl paraben, phenyl mercuric acetate, thiomerosal, and the like. Examples of osmotic agents include sorbitol, sodium chloride, and the like. Examples of gelling agents include methyl cellulose, sodium carboxymethyl cellulose, hydroxypropyl cellulose, hydroxypropyl methyl cellulose, hydroxyethyl cellulose, xanthan gum, and the like. Useful wetting agents include polysorbate 60 or 80 and other fatty esters and ethers of polyethylene glycol, quaternary ammonium salts, alkyl phenoxy polyethylene glycols, block polymers of polyethylene and polypropylene oxides, and the like.

Dextromethorphan can be formulated into a nasal solution for use as drops or as a spray, a nasal suspension, a nasal ointment, or a nasal gel. The preferred nasal dosage form is a solution which is applied as drops or an aerosol spray.

When a nasal dosage form of dextromethorphan hydrobromide is applied as an aerosol spray, a propellant gas may be added to the active ingredient and carrier composition. Suitable propellant gases include the polyhalogenated alkanes, such as trichloromonofluoromethane, $CCl_3F$ (Freon 11); dichlorodifluoromethane, $CCl_2F_2$ (Freon 12); 1,2-dichloro-1,1,2,2-tetrafluoroethane, $CClF_2CClF_2$ (Freon 114) and mixtures thereof. It may also be administered by mechanical devices without the aid of propellant gases.

The nasal antitussive compositions of this invention are prepared by procedures well known to those skilled in the art. For example, dextromethorphan hydrobromide can be added to and mixed intimately with the carrier material. The conditions under which the components of the composition are admixed will be determined, to a great extent, by the physical characteristics of the carrier in use. Where the carrier is a more or less free-flowing liquid at ordinary room temperatures, satisfactory compositions can be obtained by adding dextromethorphan to, and mixing it with, the liquid carrier at room temperature. If desired, distribution of dextromethorphan throughout the liquid carrier can be facilitated by heating the carrier prior to adding the drug thereto. Ordinarily, however, it will not be necessary to heat a carrier which is already liquid at room temperature. In any instance where heating is used, care should be taken to employ tempertures which are below that at which dextromethorphan decomposes.

The amount of dextromethorphan to carrier material used in producing the novel nasal compositions of this invention can be varied within wide limits. Conveniently, about 0.005 to 1.0 parts by weight, preferably about 0.01 to 0.20 parts by weight of dextromethorphan are used per part by weight of carrier material.

A suitable nasal dosage unit, e.g. 0.05-0.25 ml, can contain from about 1 mg to about 30 mg of dextromethorphan with a dosage of from about 1 mg to about 15 mg being preferred.

The following Examples illustrate the invention.

EXAMPLE 1

Nasal solution (drops) were prepared from the following composition:

| Ingredient | Amount |
| --- | --- |
| Dextromethorphan hydrobromide | 1.25 g |
| Polysorbate 80 | 0.05 g |
| Methyl cellulose | 0.2 g |
| Sodium chloride | 0.7 g |
| Methyl paraben | 0.1 g |
| Propyl paraben | 0.02 g |
| Sodium hydroxide to pH 7.4 | |
| Water to make | 100 ml |

The solution is prepared in the following manner:

Heat 80 ml of water to 80° C. and dissolve the parabens, sodium chloride, polysorbate 80 and dextromethorphan with stirring. The methyl cellulose is added and dispersed in the solution and then cooled at 25° C. The sodium hydroxide is added as a 0.1 Normal solution to pH 7.4, and water is added to make 100 ml of solution.

EXAMPLE 2

Aerosol solutions were prepared from the following compositions:

| | Ingredient | Amount |
| --- | --- | --- |
| (A) | Dextromethorphan hydrobromide | 10.0 g |
| | Ethanol 95% | 50.0 ml |
| | Freon 12 to make | 100 ml |
| (B) | Dextromethorphan hydrobromide | 10.0 g |
| | Propylene glycol | 25.0 ml |
| | Ethanol 95% | 25.0 ml |
| | Freon 12 to make | 100 ml |
| (C) | Dextromethorphan hydrobromide | 10.0 g |
| | PEG 400 | 17.0 ml |
| | Atmos ® 300 | 17.0 ml |
| | Propylene glycol | 17.0 ml |
| | Freon 12 to make | 100 ml |

Atmos ® 300 is a mixture of mono- and diglycerides of oleic acid.

PEG 400 is a polymer of ethylene oxide and water, represented by the formula $H(OCH_2CH_2)_nOH$ in which the average n varies from 8.2 to 9.1.

The aerosol solutions were prepared in the following manner:

The dextromethorphan hydrobromide is dissolved in the carrier solvent or mixture of solvents to form a solution. A quantity of this solution is added to a plastic coated, glass aerosol container. After cooling the container to −5° C., the propellant is added as a liquid at −15° C. A fixed volume metered valve is sealed onto the aerosol container, the unit agitated and allowed to warm to room temperature.

EXAMPLE 3

Aerosol suspensions were prepared from the following compositions:

| | Ingredient | Amount |
| --- | --- | --- |
| (A) | Dextromethorphan hydrobromide | 10.0 g |
| | Freon 114 to make | 100 ml |
| (B) | Dextromethorphan hydrobromide | 10.0 g |
| | Freon 11/12 (50/50) to make | 100 ml |

The aerosol suspensions were prepared in the following manner:

The dextromethorphan hydrobromide in its microfine state is added to a plastic coated glass container and cooled to −5° C. The propellant is added as a liquid at −15° C. and a fixed volume metered valve is attached to the container. The container is sonified in a sonic bath to aid in dispersing the dextromethorphan hydrobromide.

EXAMPLE 4

Non-aerosol sprays were prepared from the following compositions:

| | Ingredient | Amount |
| --- | --- | --- |
| (A) | Dextromethorphan hydrobromide | 10.0 g |
| | PEG 400 | 80.0 ml |
| | Ethanol 95% to make | 100 ml |
| (B) | Dextromethorphan hydrobromide | 10.0 g |
| | PEG 400 | 80.0 ml |
| | Atmos ® 300 to make | 100 ml |
| (C) | Dextromethorphan hydrobromide | 10.0 g |
| | Ethanol 95% to make | 100 ml |

The non-aerosol sprays were prepared in the following manner:

The dextromethorphan hydrobromide is added to the solvent with agitation to form a solution. The resulting solution is placed into a container fitted with a mechanically activated spray top designed to deliver a specific volume of spray.

EXAMPLE 5

An isotonic nasal solution is prepared by mixing 1.43 g of dextromethorphan hydrobromide and 0.68 g sodium chloride with sufficient distilled water to make 100 ml.

We claim:

1. A method for reducing the incidence of coughs which comprises nasally administering to a warm-blooded animal requiring antitussive therapy, a therapeutically effective amount of a compound of the formula

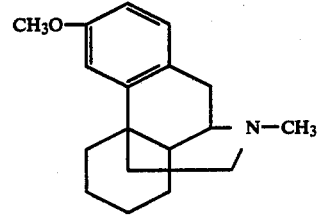

or a pharmaceutically acceptable acid addition salt thereof.

2. The method as defined in claim 1, wherein said compound is nasally administered with a nontoxic pharmaceutically acceptable nasal carrier.

3. The method as defined in claim 2 wherein the amount of dextromethorphan is about 0.005 parts by weight to about 1 part by weight per part by weight of carrier material.

4. The method as defined in claim 3 wherein the amount of dextromethorphan is about 0.01 to about 0.2 parts by weight of carrier material.

5. The method as defined in claim 2, wherein said compound is administered from a dosage form selected from the group consisting of nasal solution, nasal suspension, nasal ointment, and nasal gel.

6. The method as defined in claim 3 wherein said compound is administered from a nasal solution dosage form.

* * * * *